United States Patent [19]

Morales

[11] 4,428,385
[45] Jan. 31, 1984

[54] DEVICE FOR MEASURING MALE POTENCY

[75] Inventor: Alvaro Morales, Kingston, Canada
[73] Assignee: Queen's University of Kingston, Kingston, Canada
[21] Appl. No.: 364,485
[22] Filed: Apr. 1, 1982
[30] Foreign Application Priority Data Oct. 30, 1981 [CA] Canada ................................. 389093

[51] Int. Cl.³ ............................................... A61B 5/10
[52] U.S. Cl. .................................... 128/774; 128/694; 33/179; 33/174 D
[58] Field of Search .............. 128/694, 774, 782, 721; 33/179, 174 D

[56] References Cited

U.S. PATENT DOCUMENTS

| | | |
|---|---|---|
| 438,453 | 10/1890 | Wareham et al. ................... 33/179 |
| 766,911 | 8/1904 | Stemm ................................... 33/179 |
| 1,282,772 | 10/1918 | Dinhofer ............................... 33/179 |
| 1,357,545 | 11/1920 | De Bernyz ............................ 33/179 |
| 1,442,985 | 1/1923 | Toy ....................................... 33/179 |
| 1,672,913 | 6/1928 | Schaap ................................. 33/179 |
| 2,262,664 | 11/1941 | Bressen ................................ 33/179 |
| 2,428,980 | 10/1947 | McCann .............................. 128/721 |

Primary Examiner—Kyle L. Howell
Assistant Examiner—John C. Hanley
Attorney, Agent, or Firm—Richard J. Hicks; Stanley E. Johnson

[57] ABSTRACT

A simple and inexpensive device for measuring radial expansion of tube-like structures which is particularly useful to measure male potency. A radially expansible loop comprising a flexible, relatively slippery tube made from a material such as paper or a thermoplastic film having an elongated tail of the same or different material extending therefrom is drawn tight around the flaccid penis, by means of draw means at the end of the tail, and held in place by an adhesive patch. Should an erection occur the tail slides partially out of the tube to accommodate the radial expansion which occurs and remains in the extended position until manually retracted by pulling the draw means at the end of the tail. The radial expansion can be assessed by measuring the extension of the tail exposed.

8 Claims, 5 Drawing Figures

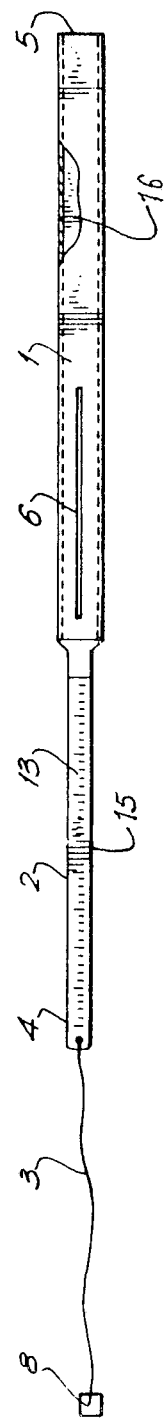
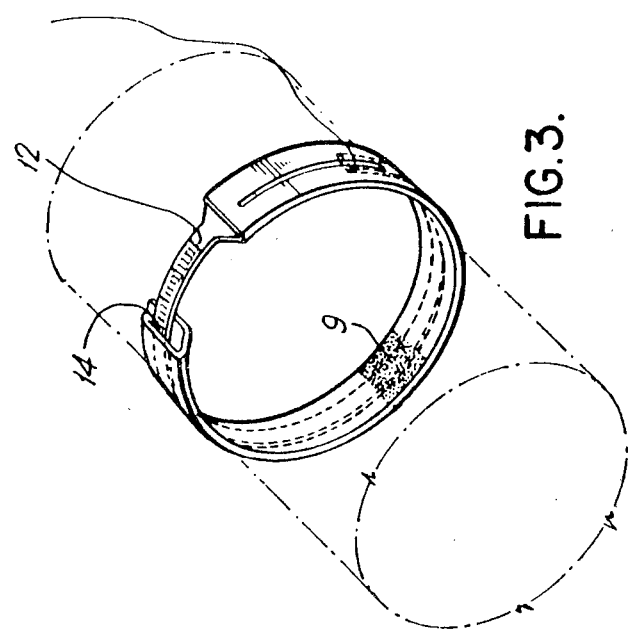
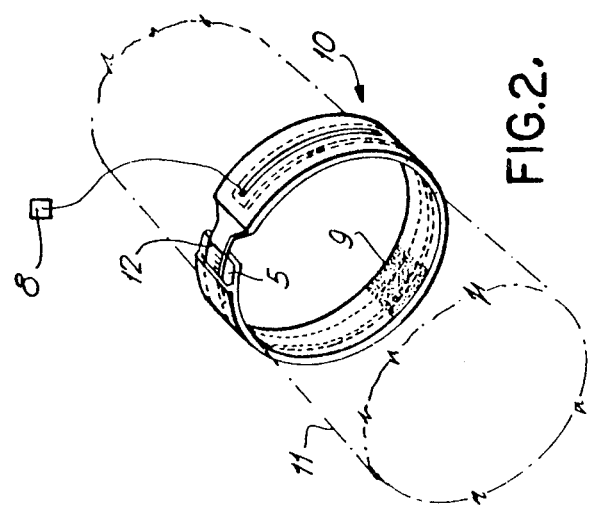

DEVICE FOR MEASURING MALE POTENCY

FIELD OF INVENTION

This invention relates generally to a device for monitoring radial expansion in elastically expansible tube-like structures and more particularly relates to a device for monitoring radial expansion of a human penis.

BACKGROUND OF INVENTION

Impotence in the human male may be defined as the inability of the patient to achieve and/or sustain sufficient erection of the penis to permit sexual intercourse to be completed. Impotence is a surprisingly prevalent complaint among the adult male population and it is known that several different physiological and psychological factors may cause or influence impotence. In order to be able to treat the impotent patient it is of primary importance for the physician to determine whether the symptoms are physiological or psychological in origin. It is known that the normal male has three or four spontaneous erections of varying degrees during the course of a normal night's sleep so that if it can be determined whether or not the impotent patient is physically capable of an erection under rest conditions, the physician will have made a considerable advance in his diagnosis. Clearly as the patient is asleep, he cannot monitor his own bodily functions and heretofore the only way to make the required determination has been by measurement of penile expansion with mercury-in-rubber gauges connected to a polygraph. This equipment is expensive and the procedure cumbersome. Experience has shown that a minimum of three nights testing is required for reliable results and this is, therefore, a time consuming and expensive form of testing.

OBJECTS OF THE INVENTION

It is an object of the present invention to provide a simple inexpensive and self administered monitoring device to detect and measure the extent of erection of a penis.

Another object of the present invention is to provide a simple monitoring device to detect radial expansion which may occur in elastic tubular structures under pressure.

BRIEF DESCRIPTION OF THE INVENTION

Thus, by one aspect of the invention there is provided a device for monitoring radial expansion in an elastically expansible tube-like structure comprising:

an elongated thin walled tubular member made from a flexible but relatively inelastic material such as paper or a thermoplastic, and including hole means in the wall adjacent one end thereof;

a flexible, relatively inelastic tail member extending longitudinally from said one end of said tubular member; and a draw pull means at the free end of said tail member;

a substantial portion of said tail being arranged for sliding movement within said tubular member by inserting the free end thereof through the other end of said tubular member, with said draw pull means projecting outwardly through said hole means, so as to provide a radially expansible closed loop which can be drawn tightly around said tube-like structure.

By a preferred aspect of the invention there is provided a device for measuring male potency, similar to that described above which is arranged to encircle a penis so as to measure the degree of erection thereof.

DESCRIPTION OF THE DRAWINGS

The invention will be described in more detail hereinafter with reference to the drawings in which:

FIG. 1 is a top view of one embodiment of the device according to the invention;

FIG. 2 is a diagramatic sketch of the device of FIG. 1 in operative position on a radially expansible tube, in the contracted condition;

FIG. 3 is a diagramatic sketch of the device of FIG. 1 in operative position on a radially expanded tube;

DETAILED DESCRIPTION OF THE INVENTION

Figure 4:
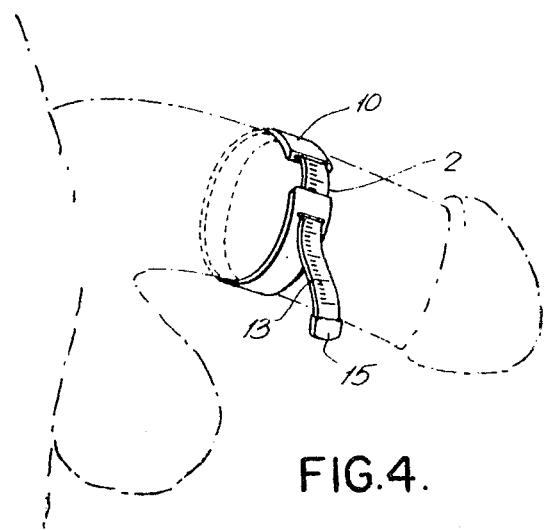
FIG. 4 is a diagramatic sketch of an alternative embodiment of the invention in operative position on a flaccid penis.
Figure 5:
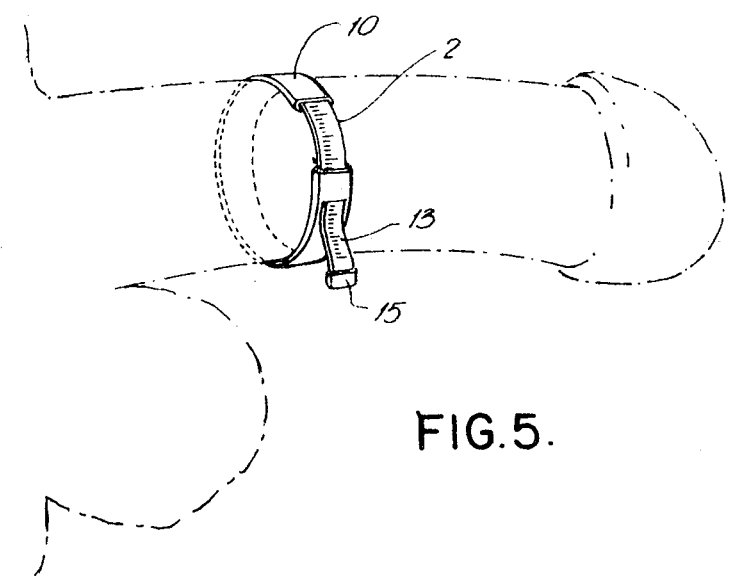
FIG. 5 is a diagramatic sketch of the embodiment of FIG. 4 in position on an erect penis.

As seen in FIG. 1, the device comprises an elongated flattened, thin walled, tubular strip 1 having an elongated, generally single layer, tail 2 extending longitudinally therefrom. Optionally the tail 2 is provided with a thin pull string 3 at the end 4 thereof with a tab 8 at the free end thereof. Alternatively, as shown in FIGS. 4 and 5, tail 2 may be provided with a tab 15 and the string 3 omitted. The end 4 of tail 2 and string 3 is inserted through open end 5 of tubular portion 1 and the pull string 3 (or free end tail 2 and tab 15) is withdrawn from the tubular portion through a hole or slit 6 provided for that purpose, thereby forming the device into a closed radially expansible loop 10. The tubular portion 1 and tail 2 are preferably made of a thin flexible, relatively slippery but inelastic, thermoplastic material, such as polyethylene, in order to minimize friction between the tubular portion and the tail. It will, of course, be appreciated that the material employed is not critical and any suitable flexible sheet or film like material may be employed, including paper, plastic coated paper, and any of the commonly known thermoplastic film materials. Nor it is essential that the tubular portion 1 and tail portion 2 be fabricated from the same material, it being contemplated that tubular portion 1 may be fabricated from a thermoplastic material and tail portion 2 from paper or the like or vice versa. All that is necessary is that the coefficient of friction between the tubular portion 1 and the tail 2 is sufficiently low, at least in the expansile direction, to permit relatively easy movement of the tail 2 relative to the tube 1. It is further contemplated, within the scope of this invention that the sliding surfaces of the tubular portion 1 and tail 2 may be coated, embossed or otherwise treated to provide one-way slip only in the expansile direction so as to ensure measurement of maximum expansion only, without risk of some subsequent contraction or retraction. Such one-way slip treatment would include embossing to provide a fish scale like surface on both parts, or coating with a directionally laid fibrous material (15,16) in known manner.

In order to use the invention the closed loop 10 is passed over the end of the unexpanded tube (FIG. 2) or flaccid penis (FIG. 4) 11, or otherwise formed in situ around the tube 11, and drawn into circumferential contact therewith by pulling string 3 or tab 15 to tighten the loop. In order to hold the loop in position a portion 9 of the inner periphery may be coated with a pressure sensitive adhesive, such as that used in a "Band-Aid" ® first aid dressing, or a piece of "Band-Aid" ® may be employed for that purpose. The position 12 of the tail 2 relative to the end 5 of the tubular portion is noted either by marking directly on tail 2 with any suitable pen, or by noting the position on a scale 13 optionally provided on tail 2. If penile erection occurs spontaneously while the patient is asleep in the preferred embodiment (FIG. 5), or if excess pressure in the elastic tube or pipe occurs at any time (FIG. 3), in the alternative embodiment, radial expansion of the penis or tube occurs and the loop 10 expands, as shown in FIG. 3, to its extended position 14 where it remains until removed or a later erection or pressure surge enlarges it still further. The maximum expansion can therefore be read on scale 13 or by direct measurement of the distance between points 12 and 14. It will be appreciated that the measurement of maximum expansion is of considerable value in determining the degree of erection which in turn is a measure of potency in the preferred embodiment, or to determine whether limiting or safety factors have been exceeded in the alternative embodiment.

I claim:

1. A device for monitoring penile expansion comprising:
    an elongated thin walled tubular member having first and second ends and made from a soft and flexible but inelastic material, and including hole means in the wall adjacent said first end thereof;
    a soft and flexible but inelastic tail member extending longitudinally from said first end of said tubular member and terminating with a draw pull means;
    said tail member being insertable axially into said tubular member at said second end with said draw pull means projecting outwardly through said hole means thereby arranging a substantial portion of said tail within said tubular member for sliding movement relative thereto so as to provide a closed loop which is freely radially expansible in response to erectile activity of a flaccid penis about which said loop is tightly drawn.

2. A device as claimed in claim 1 including scale means on said tail member arranged to measure radial expansion of said closed loop.

3. A device as claimed in claim 1 including adhesive means on at least a portion of the inner periphery of said closed loop, to secure said loop in a selected longitudinal position on said penis.

4. A device as claimed in claim 1 wherein said draw pull means comprises a draw string secured to the terminal end of the tail member.

5. A device as claimed in claim 1 wherein said draw pull means comprises a tab at the terminal end of the tail member.

6. A device as claimed in claim 1 wherein said tubular member and said tail member are fabricated from materials selected from the group comprising paper, plastic coated paper and thermoplastic film material.

7. A device as claimed in claim 6 wherein said tubular member and said tail member are fabricated from different said selected materials.

8. A device as claimed in claim 6 or 7 wherein said tubular member and said tail member include means to provide one-way slip therebetween in the expansile direction.

* * * * *